United States Patent
Lander

(10) Patent No.: US 12,419,935 B2
(45) Date of Patent: Sep. 23, 2025

(54) EXOSOMES FOR THE TREATMENT OF INTERSTITIAL CYSTITIS

(71) Applicant: Elliot B. Lander, Rancho Mirage, CA (US)

(72) Inventor: Elliot B. Lander, Rancho Mirage, CA (US)

( * ) Notice: Subject to any disclaimer, the term of this patent is extended or adjusted under 35 U.S.C. 154(b) by 0 days.

(21) Appl. No.: 17/845,067

(22) Filed: Jun. 21, 2022

(65) Prior Publication Data

US 2023/0027827 A1 Jan. 26, 2023

Related U.S. Application Data

(60) Provisional application No. 63/224,861, filed on Jul. 23, 2021.

(51) Int. Cl.
*A61K 38/18* (2006.01)
*A61K 9/00* (2006.01)
*A61K 35/28* (2015.01)

(52) U.S. Cl.
CPC ........ *A61K 38/1808* (2013.01); *A61K 9/0019* (2013.01); *A61K 35/28* (2013.01)

(58) Field of Classification Search
None
See application file for complete search history.

(56) References Cited

U.S. PATENT DOCUMENTS

| 10,869,916 B2 | 12/2020 | Ichim | |
|---|---|---|---|
| 2018/0042847 A1* | 2/2018 | Ross | A61K 38/18 |
| 2020/0163998 A1 | 5/2020 | Park | |

FOREIGN PATENT DOCUMENTS

| EP | 3 402 489 B1 | 6/2021 |
| WO | 2018102397 A1 | 7/2018 |

OTHER PUBLICATIONS

Yu et al. Exosomes Derived from Mesenchymal Stem Cells. Int J Mol Sci. Mar. 2014; 15(3): 4142-4157 (Year: 2014).*
Sairanen et al. Potassium Sensitivity Test (PST) as a Measurement of Treatment Efficacy of Painful Bladder Syndrome/Interstitial Cystitis: A Prospective Study With Cyclosporine A and Pentosan Polysulfate SodiumNeurourol Urodyn. 2007;26(2):267-70. (Year: 2007).*
Cvach & Rosamilia. Review of intravesical therapies for bladder pain syndrome/interstitial cystitis Transl Androl Urol. Dec. 2015; 4(6): 629-637 (Year: 2015).*
Higashiyama et al. A Heparin-Binding Growth Factor Secreted by Macrophage-Like Cells That Is Related to EGF. Science. Feb. 22, 1991;251(4996):936-9. (Year: 1991).*
Andersson and Arner.A Heparin-Binding Growth Factor Secreted by Macrophage-Like Cells That Is Related to EGF (Physiol Rev. Jul. 2004;84(3):935-86 (Year: 2004).*
Woo et al.A Heparin-Binding Growth Factor Secreted by Macrophage-Like Cells That Is Related to EGFThe Journal of Urology Mar. 2011; 185(6): 1132-1138 (Year: 2011).*
Kim et al.Stem Cell Therapy for Interstitial Cystitis/Bladder Pain Syndrome. Curr Urol Rep (2016) 17: 1 (Year: 2016).*
Xo Glo Purified MSC Exosomes. Kimera Exosomes (obtained from https://shop.exosomes.com/products/xoglo-pro on Oct. 26, 2023) (Year: 2019).*
Chen et al. Inflammatory responses and inflammation-associated diseases in organs. Oncotarget. Jan. 23, 2018; 9(6): 7204-7218. Published online Dec. 14, 2017. (Year: 2017).*
Treating interstitial cystitis. Harvard Health. (accessed at: https://www.health.harvard.edu/diseases-and-conditions/treating-interstitial-cystitis) (Year: 2017).*
Lusty et al. Treatment effectiveness in interstitial cystitis/bladder pain syndrome: Do patient perceptions align with efficacy-based guidelines?. Can Urol Assoc J. Jan. 2018; 12(1):E1-E5. (Year: 2018).*
Chimenti et al. A Mechanism-Based Approach to Physical Therapist Management of Pain. Phys Ther. May 1, 2018;98(5):302-314. (Year: 2018).*
Adamowicz et al. Conditioned medium derived from mesechymal stem cells culture as a intravesical therapy for cystis interstitials; Medical Hypothesis-XXX Medical Hypotheses 82 (2014) 670-673.
Arabpour; Anti-inflammatory and M2 macrophage polarization-promoting effect of mesenchymal stem celll-derived exosomes; International Immunopharmacology; vol. 97 (Aug. 2021) (abstract only).
Huang; Reply to the Commentary on "New Frontiers or the Treatment of Interstitial Cystis/Bladder Pain Syndrome-Focused on Stem Cells, Platelet-Rich Plasma, and Low-Energy Shock Wave"; Int Neurol J 2020; 24(4):389-390.
Lander; Personal cell therapy for interstitial cystitis with autologous stromal vascular fraction stem cells; Ther Adv Urol 2019, vol. 11; 1-9.
Sarvar; Mesenchymal Stem Cell-Derived Exosomes: New Opportunity in Cell-Free Therapy; Adv Pharm Bull, 2016 6(3), 293-299.

* cited by examiner

*Primary Examiner* — Marcia S Noble
*Assistant Examiner* — Briana N Ebbinghaus
(74) *Attorney, Agent, or Firm* — TMB Law; Timothy M. Brown

(57) ABSTRACT

The invention provides a method of treating interstitial cystitis that applies therapeutic exomes to the bladder of a patient through intravesical administration. Unlike the intravesical administration of stem cells, the intravesical administration of exosomes permits a therapeutic amount of paracrine-active growth factors and cytokines to be applied to bladder tissue before they can voided by urination.

6 Claims, No Drawings

EXOSOMES FOR THE TREATMENT OF INTERSTITIAL CYSTITIS

CROSS-REFERENCE TO RELATED APPLICATION

This application claims priority to Provisional Application No. 63/224,861 filed Jul. 23, 2021, the entire contents of which are incorporated herein by reference for all purposes.

FIELD OF THE INVENTION

The invention is in the field of bladder conditions and their treatment.

BACKGROUND OF THE INVENTION

Interstitial Cystitis (IC) is a chronic bladder condition resulting in recurring discomfort or pain in the bladder and surrounding pelvic region. People with IC usually have inflamed or irritated bladder walls which can cause scarring and stiffening of the bladder.

IC affects men and women of all racial and ethnic backgrounds and ages. However, it is more common in women than men. Early research suggested that IC ranged from 1 out of every 100,000 to 5.1 out of every 100,000 in the general population, but updated epidemiologic research conducted in 2006 suggests that up to 12% of women may have early symptoms of IC.

The cause of IC is currently unknown. Its diagnosis is often made only after excluding other urinary bladder causes. Symptoms of IC include frequent urination, a feeling of urgency to urinate, feeling of abdominal or pelvic pressure, tenderness, intense pain in the bladder, pelvic, or vaginal region, and severe lower abdominal pain that intensifies as the urinary bladder fills or empties.

Oral medications may improve the signs and symptoms of IC, and include nonsteroidal anti-inflammatory drugs, such as ibuprofen or naproxen sodium, opiates, tricyclic antidepressants, such as amitriptyline or imipramine, antihistamines, such as loratadine and pentosan polysulfate sodium, and bladder relaxants such as Ditropan™ or Detrol™. Non nonsteroidal anti-inflammatory drugs function to relieve pain associated with IC, while tricyclic antidepressants help relax the bladder and block pain. Bladder relaxants attempt to increase bladder capacity and decrease frequency. Antihistamines may reduce urinary urgency and frequency, and relieve some other IC symptoms. Pentosan polysulfate sodium, which is approved by the USFDA for treating interstitial cystitis, has an unknown mechanism of action, but may restore the inner glycosaminoglycan surface of the bladder and protect the bladder wall from irritating substances in the urine. Pentosan polysulfate sodium may take two to four months to relieve pain, and up to six months to decrease urinary frequency.

While current medications provide some relief in treating the symptoms of IC, they do not provide a long-term treatment alternative and do not address the cause of IC. Moreover, current medications are effective in treating only a few of the symptoms of IC and do not provide a wide-spectrum therapy.

Mesenchymal stem cell (MSC) therapy has shown promise in treating a wide variety of conditions. Research suggests that MSC may be a potential therapy for the treatment of IC. However, these therapies involve the injection of MSC into the bladder wall or its surrounding tissue, or intravenous administration.

While showing possible efficacy for the treatment of IC, MSC therapy would not likely lend itself to intravesical administration. Due to the intercellular tight junctions of the urothelium and size of MSC, MSC administered intravesicaly are prevented from migrating into the uroepithelium.

What is needed in the art therefore is a wide-spectrum therapeutic for treating IC that can be administered intravesicaly to administer a cell-based therapeutic directly to the urothelium.

SUMMARY OF THE INVENTION

The inventor surprisingly discovered that MSC exosomes can provide a wide-spectrum therapeutic capable of being administered directly to the urothelium in the treatment of IC. The inventor discovered that MSC exosomes can produce a therapeutic, paracrine effect and do not face the same size limitations of MSC in traversing the urothelium. Thus, MSC exosomes can be administered intravesicaly in a therapeutic amount without the limitation of being eliminated before traversing the urothelium.

It is therefore an object of the invention to provide a method of treating IC, comprising administering to a patient in need thereof a therapeutically effective amount of exosomes.

In some aspects, the exosomes are isolated.

In some aspects, the exosomes have a mean diameter of between about 15 nm and about 200 nm.

In some aspects, the exosomes are obtained from MSC, induced pluripotent stem cell (iPS), stem cells from adipose stromal vascular fraction (SVF), or a combination thereof.

In some aspects, the MSC are one or more of birth tissue MSC, bone marrow MSC, peripheral blood derived MSC, and adipose MSC.

In some aspects, the birth tissue is placenta, amniotic fluid, or a combination thereof.

In some aspects, the method further comprises administering to the patient a therapeutic amount of stem cells.

In some aspects, the stems are MSCs, iPS, SVF stem cells, or a combination thereof.

In some aspects, the MSCs are from birth tissue, bone marrow, peripheral blood derived MSC, adipose, or combinations thereof.

In some aspects, the stem cells are administered intravenously, to the pelvic floor, to the bladder muscle, intravesically, or a combination thereof.

In some aspects, the stem cells are autologous or allogeneic.

DETAILED DESCRIPTION

Stem cell therapy has shown great potential in treating a variety of conditions, including IC. However, the size of stem cells prevents them from traversing the tight junctions of the cells of the urothelium. Thus, intravesical administration of a stem cell therapeutic remained impractical prior to the invention.

The inventor surprisingly discovered that stem cell exosomes can provide a stem cell-based therapeutic capable of intravesical administration. The inventor discovered that stem cell exosomes do not present the size exclusion limitations of stem cells and can traverse the urothelium. Thus, the exosomes of the invention can be administered intravesically and traverse the urothelium before they are voided by the patient. This not only allows the therapeutic to be easily administered directly to the tissue affected by IC, it also provides a large dose of paracrine-active growth factors and chemokines and mRNA that would otherwise require time to be secreted by whole stem cells that are administered to the body.

In one non-limiting embodiment, the invention provides a method of treating IC comprising intravesicaly administering to a patient a therapeutically effective amount of exosomes. The exosomes can be obtained from a conditioned culture medium that has been used for the in vitro culture of MSC, iPS cells, SVF stem cells, or a combination thereof. The exosomes can similarly be obtained from MSC from a tissue explant without expanding the MSC in culture prior to obtaining the exosomes. The tissue explant can be a fresh tissue preparation, or cryopreserved tissue preparation. MSC can be obtained from tissue explants of bone marrow or peripheral blood, for example. The MSC can be stromal MSC. In some embodiments, the exosomes are isolated. Suitable exosomes for use with invention and their methods of manufacture include those disclosed in U.S. Patent Application Publication No. 2020/0163998, the entire contents of which is incorporated herein by reference for all purposes. The exosomes can be XoGloPro® exosomes from Kimera®.

Tissue sources for MSC for providing exosomes for use with the invention include, but are not necessarily limited to, bone marrow, umbilical cord, umbilical cord membrane, umbilical cord blood, placenta, Wharton's jelly, amniotic fluid, peripheral blood, adipose, decidua basalis, ligamentum flavum, dental pulp, breast milk, adipose tissue, or combinations thereof. The MSC can be autologous, allogeneic, or a combination thereof. The exosomes can be obtained from a primary culture of stem cells. In some embodiments, the exosomes are obtained from an MSC clone or a combination of MSC clones. The exosomes can be obtained from a culture of cells that has been treated with one or more growth factors, one or more cytokines, one or more hormones, or combinations thereof. For example, the exosomes can be obtained from a culture of MSCs that has been stimulated by IFNγ (IFNγ-Exo) such as disclosed by Riazifar et al. (Stem Cell-Derived Exosomes as Nanotherapeutics for Autoimmune and Neurodegenerative Disorders; *ACS Nano* 2019, 13, 6, 6670-6688), the entire contents of which are incorporated herein by reference for all purposes.

The exosomes can be obtained from an exosome preparation. As used herein, the phrase "exosome preparation" refers to a suspension containing exosomes, and includes, but is not necessarily limited to, cell lysates and supernatants of cellular conditioned medium. In some embodiments, the exosomes are isolated. Suitable methods for isolating exosomes from an exosome preparation include, but are not necessarily limited to, ultracentrifugation, sucrose gradient ultracentrifugation, high performance liquid chromatography (HPLC), ultrafiltration, and exosome precipitation, such as precipitation by polyethylene glycols (PEGs).

In a preferred embodiment, the exosomes have a size capable of traversing the urothelium of a patient having IC. The exosomes can have a mean diameter that is between about 15 nm and about 120 nm, between about 30 nm and about 120 nm, between about 15 nm and about 200 nm, or between about 30 nm and about 200 nm. As used herein, the term "about" includes the value that is referenced, or that varies (plus or minus) by up to 5%, up to 10%, up to 15%, or up to 20% of the stated value. Exosomes of a desired size can be obtained by, for example, subjecting an exosome preparation to filtration or size exclusion chromatography. The exosome preparation can be subjected to filtration or size exclusion chromatography one, two, three, for or more times. In some embodiments, the exosome preparation is subjected to filtration or size exclusion chromatography between 1 and 100 times. Suitable filters for obtaining exosomes having a desired size include, but are not limited to, polycarbonate membrane filters.

In some embodiments, the exosomes contain one or more growth factors, one or more cytokines, mRNAs, miRNAs, and non-coding RNAs. The growth factors or cytokines can include heparin-binding epidermal growth factor—like growth factor (HB-EGF), keratinocyte growth factor (KGF), basic fibroblast growth factor (bFGF), platelet-derived growth factor (PDGF), insulin-like growth factor (IGF), or combinations thereof. The growth factors in the exosomes can be exogenous or endogenous. The exosomes can contain exogenous growth factors and/or cytokines as a result of loading the exosomes with one or more growth factors and/or cytokines in vitro, such as by electroporation, for example. The exosomes can contain endogenous growth factors and/or cytokines as a natural result of cellular processes during in vitro culture. In some aspects, the exosomes contain endogenous cytokines and/or growth factors as a result of the stem cells from which they are produced being transfected to with a desired growth factor and/or cytokine. For example, a stem cell can be transfected to express a desired growth factor and/or cytokine in exosomes secreted by the stem cell, wherein transfecting the stem cell with the desired growth factor or cytokine leads to the expression of a growth factor and/or cytokine that would not otherwise be expressed within exosomes produced by the stem cell. Similarly, a stem cell can be transfected with a desired growth factor and/or cytokine that is naturally expressed in exosomes secreted by the stem cell, wherein transfecting the stem cell with the desired growth factor and/or cytokine results in an increased expression of the desired growth factor and/or cytokine in the stem cell's exosomes.

The method of the invention can be practiced by administering to a patient in need thereof a therapeutically effective amount of exosomes. The exosomes can be administered intravesically, intravenously, by injection into the pelvic floor, injection into the bladder muscle, or combinations thereof. Intravesical administration can be practiced by intravesical instillation of a therapeutically effective amount of exosomes directly into the bladder of a patient via a urethral catheter or by suprapubic injection with or without radiographic guidance. The exosomes can be administered once or repeatedly. The exosomes can be administered at a dose of about 15 billion exosomes. In some embodiments, the exosomes can be administered at a dose of at least about a trillion exosomes.

In some embodiments, the method further comprises administering a therapeutically effective amount of stem cells to the patient. The stem cells can be MSC, SVF stem cells, iPS, or a combination thereof. The MSC can be stromal MSC. The MSC can be obtained from bone marrow, umbilical tissue, placenta, amniotic fluid, peripheral blood, adipose, or combinations thereof. The stem cells can be autologous, allogeneic, or a combination thereof. The stem cells can be administered once or repeatedly. Exosomes can be administered to the patient before one or more administrations of stem cells, concurrently with one or more administrations of stem cells, of after the patient receives one or more administrations of stem cells. For example, exosomes can be administered one or more times to the patient after the patient receives at least one administration of stem cells that does not sufficiently address the patient's IC or IC symptoms.

The exosomes and stem cells can be suspended in a pharmaceutically acceptable carrier or excipient prior to administration to a patient. Suitable pharmaceutical carriers and excipients for use with the invention include, but are not necessarily limited to those disclosed in the following publications, the entire contents of which are incorporated herein by reference for all purposes: Remington: The Science and Practice of Pharmacy, 19$^{th}$ Ed (Easton, Pa.: Mack Publishing Company, 1995); Hoover, John E., Remington's Pharmaceutical Sciences, (Easton, Pa.: Mack Publishing Co 1975); Liberman, H. A. and Lachman, L., Eds., Pharmaceutical Dosage Forms (New York, N.Y.: Marcel Decker 1980); and Pharmaceutical Dosage Forms and Drug Delivery Systems, Seventh Ed (Lippincott Williams & Wilkins 1999).

The method can be practiced to treat a patient that has IC, wherein administering exosomes, with or without stem cells as disclosed herein, reverses or inhibits the progression of IC and/or its symptoms. The patient can be at risk of developing IC, wherein administering exosomes, with or without stem cells as disclosed herein, prevents the development of IC and its symptoms. Practicing the method can prevent or inhibit one or more IC symptoms in the patient, including bladder pressure, pain in the lower back, pelvis or urethra, vaginal pain, pain during or after intercourse, and frequent urination.

EXAMPLE

The following case reports are provided as an example of the inventive method and are not to intended to limiting. One skilled in the art will appreciate that modifications can be made to the treatments exemplified below without departing from the scope of the invention. References to exosomes refer to Kimera® XoGloPro® isolated exosomes derived from placental mesenchymal stem cells.

Case Report for Patient 1 (Pain Went from 5/10 to 1/10)

31 year old female presented with IC for several years.

Patient complained of abdominal bloating, both daytime and nighttime frequency, severe internal pelvic pain radiating to coccyx, and recent flare ongoing for nearly 1 year.

SVF (IV and pelvic floor) (no exosomes used)

Good response to SVF within 1 month and 6 months later pain decreased significantly.

Patient was still using Elmiron™ but on much lower dose.

Nocturia gone at 6 months evaluation.

Patient wanted additional treatment but had to leave the country for a year.

18 months later symptoms improvement persisted and patient requested a repeat procedure.

Patient had repeat SVF deployment (IV and pelvic floor) with addition of 5B intravesical exosomes.

Approximately three weeks later, patient felt significantly better but still had some minor irritation in the bladder so another 5B intravesical exosomes were instilled.

All bladder symptoms and pain quickly went away and patient requested one more dose of exosomes prophylactically before leaving the country again so 15B exosomes were instilled intravesicaly.

Patient nearly 3 months since requiring oral Elmiron™ and patient continues to be pain free.

Some abdominal bloating persists related to SIBO.

Case Report for Patient 2 (Pain Decreased from 9.5/10 to 0/10)

56 year old healthy Hispanic female.

Patient complained of severe frequency and suprapubic pain, severe pelvic floor spasm causing intermittent urinary retention on self-catheterization. Patient also had large bladder diverticulum which makes emptying difficult.

Patient stated symptoms had been present non-stop since she experienced a UTI.

Patient was under care for IC at a local university where she was being offered cystectomy and urinary diversion for "end stage" recalcitrant IC. She was receiving urethral dilation, instillation therapies, narcotics, and intravesical Botox among other treatments.

Patient had history of bladder diverticulum and was scheduled at Loma Linda University for pre cystectomy urodynamics and radiographic cystogram which she completed and was evaluated.

SVF (IV and pelvic floor) and patient received 5B intravesical exosomes.

Patient had complete absence of pain for 3 weeks post treatment (pain went from 8-9/10 to 0) and then noted mild bladder pain (1 or 2/10) for a few days at week 4 and she presented for follow-up visit.

Week 4 visit-5B intravesical exosomes administered and all residual pain went away within 24 hours.

Patient requested more intravesical exosomes for "prevention" and another 5B were instilled intravesicaly.

Bladder pain resolved and continues to be "0" out of 10. Patient was able to fully discontinue Elmiron™ after her first SVF treatment and off for 8 months.

Patient states bladder pain recurred for prior 2 weeks following severe UTI with resistant organism (which appears to have triggered IC again). Repeat stem cell (expanded cells) and 5B intravesical exosome deployments performed.

Patient remains pain free 4 weeks later.

Case Report for Patient 3 (Unable to Assess Pain Score Since Pain is Sporadic and Variable)

65 year old female with stabbing vaginal pain and night time frequency×12.

Treated with SVF (IV and pelvic floor) and 5B intravesical exosomes into bladder.

Patient also elected for cryopreservation of personal stem cells.

Severe pelvic pain for 2 months after treatment.

Now using less opioids but overall bouts of severe pain is about the same.

Night frequency slightly less and now at 6-12×.

Patient now has sporadic intervals of being pain free for as much as 2 weeks.

Case Report for Patient 4 (Pain Decreased from 7.5/10 to 1/10)

52 year old female with severe IC×10 years.

Patient received SVF (IV and pelvic floor) and 15B intravesical exosomes.

Patient also elected for cryopreservation of personal stem cells.

Pain went down to 4.5 by 3 weeks and then to level 1 at 6 weeks and patient remains in only mild discomfort.

Case Report for Patient 5 (Pain Decreased from 8/10 to 2/10)

43 year old female with 8 years of supra-pubic and anterior vaginal pain with some frequency of voiding.

Patient received SVF (IV and pelvic floor) in addition to 15B intravesical exosomes.

Within 3 weeks, pain and pressure resolved and patient was able to have intercourse for first time in years.

Only mild discomfort and some bloating persists.

The invention claimed is:

1. A method of treating interstitial cystitis, comprising:
administering a therapeutically effective amount of stromal vascular fraction stem cells to the pelvic floor and intravenously to a patient in need thereof; and
intravesicaly administering to said patient a therapeutically effective amount of isolated exosomes derived from placental mesenchymal stem cells;
wherein administering said stromal vascular fraction stem cells and said exosomes treats in said patient at least one of frequency of urination, internal pelvic pain, suprapubic pain, vaginal pain, pain in the urethra, pain in the lower back, pain during or after intercourse, or combinations thereof.

2. The method of claim 1, wherein said exosomes do not comprise an exogenous therapeutic agent.

3. The method of claim 1, wherein said exosomes have a mean diameter of between about 15 nm and 120 nm, or between about 15 nm and 200 nm.

4. The method of claim 1, wherein said exosomes comprise heparin-binding epidermal growth factor-like growth factor (HB-EGF) mRNA, HB-EGF protein, or a combination thereof.

5. The method of claim 4, wherein a portion of at least one of said HB-EGF mRNA and said HB-EGF protein is exogenous.

6. The method of claim 1, wherein said stromal vascular fraction stem cells are autologous stem cells, allogeneic stem cells, or a combination thereof.

* * * * *